United States Patent [19]

Penner et al.

[11] Patent Number: 5,773,702
[45] Date of Patent: Jun. 30, 1998

[54] IMIDAZOLINONE HERBICIDE RESISTANT SUGAR BEET PLANTS

[75] Inventors: Donald Penner, Williamston; Terry R. Wright, Lansing, both of Mich.

[73] Assignee: Board of Trustees operating Michigan State University, East Lansing, Mich.

[21] Appl. No.: 682,303

[22] Filed: Jul. 17, 1996

[51] Int. Cl.$^6$ .......................... C12N 15/01; C12N 15/05; A01H 3/00; A01H 4/00

[52] U.S. Cl. .................... 800/230; 800/200; 800/DIG. 9; 435/240.4; 435/240.45; 435/240.54; 435/419; 47/58

[58] Field of Search .......................... 435/240.4, 240.45, 435/240.46, 240.47, 240.48, 240.49, 240.5, 240.54, 419; 47/58; 800/200, 230, DIG. 9

[56] References Cited

U.S. PATENT DOCUMENTS

| | | | |
|---|---|---|---|
| 5,013,659 | 5/1991 | Bedbrook et al. | 435/172.3 |
| 5,141,870 | 8/1992 | Bedbrook et al. | 435/320.1 |
| 5,378,824 | 1/1995 | Bedbrook et al. | 536/23.6 |

FOREIGN PATENT DOCUMENTS

| | | | |
|---|---|---|---|
| 375875 | 4/1990 | European Pat. Off. | C12N 15/52 |

OTHER PUBLICATIONS

Hart, et al., Weed Science 40:378–383 (1992).
Hart et al., Weed Science 40:317–324 (1993).
Current Protocols in Molecular Biology, J. Wiley and Sons, New York (1991).
Saunders, et al., in Crop Science 32:1357–1360 (1992).
Newhouse et al., Theoretical and Applied Genetics 83:65–70 (1991).
Ray, Plant Physiol. 75:827–831 (1984).
Shaner, et al., Plant Physiol. 76:545–546 (1984).
Westerfield, J. Biol. Chem. 16:495–502 (1945).
Bradford, Anal. Biochem. 72:248–254 (1976).
Bernasconi et al., J. Biol. Chem. 270:17381–17385 (1995).
Renner and Powell, Weed Technology 5:622–627 (1991).
MSU Weed Control Guide (1997).
Newhouse, K.E., Plant Physiol 100:882–886 (1992).

*Primary Examiner*—Douglas W. Robinson
*Assistant Examiner*—Thomas Haas
*Attorney, Agent, or Firm*—Ian C. McLeod

[57] ABSTRACT

Sugar beet plants which are resistant to imidazolinone herbicides are described. The sugar beet plants are derived from susceptible cells by selection for mutant imidazolinone resistant cells with the herbicide. The resistant plants derived from the cells can be grown in fields where imidazolinones have been used for weed control.

14 Claims, 4 Drawing Sheets

IMIDAZOLINONE HERBICIDE RESISTANT SUGAR BEET PLANTS

BACKGROUND OF THE INVENTION

(1) Summary of the Invention

The present invention relates to a method for producing sugar beet plants (Beta vulgaris L.) which are resistant to imidazolinone herbicides used for weed control. In particular, the present invention relates to sugar beet plants derived from a susceptible sugar beet by selection for a mutation of a gene encoding acetolactate synthase (ALS), also known as acetohydroxyacid synthase (AHAS), using the herbicide with cells in a culture medium.

(2) Description of Related Art

The prior art has described the genetic alteration of the acetolactate synthase gene by recombinant means as shown by U.S. Pat. Nos. 5,013,659; 5,141,870 and 5,378,824 to Bedbrook et al. This type of modification in sugar beet plants is shown by Example IV of the '824 patent. The results were less than satisfactory in producing plants which bred true for the herbicide resistance.

Various resistant plants were produced and cross breed. Saunders et al. in Crop Science 32:1357–1360 (1992) also describe the production of the sugar beet plant (CR1-B) which is resistant to sulfonylureas from the susceptible self-fertile clone (REL-1) by selection for mutant cells in a culture medium containing the herbicide. Various resistant plants were produced and cross-bred. Hart et al. (Weed Sci. 40:378–383 (1992); and Weed Sci. 41:317–324 (1993)) further characterized the resistant line and determined that resistance was due to altered ALS activity and showed no cross resistance to other ALS-inhibiting herbicides, and was coded for by a single, semidominant gene.

There are no publications describing imidazolinone resistance obtained by modifying ALS or AHAS in sugar beet plants. Various corn lines with this resistance have been developed as described by Newhouse et al. Theoretical and Applied Genetics 83:65–70 (1991).

A commercial route to crop protection is the use of "safeners" such as described in European Patent No. 375,875. This method introduces another chemical into the soil. The preferred method is to develop sugar beet plants which are resistant to the imidazolinone herbicides.

OBJECTS

It is therefore an object of the present invention to provide a method for imparting resistance to imidazolinone herbicides in sugar beet plants by selection for a mutation of a acetolactate synthase gene encoding for this resistance. Further, it is an object of the present invention to provide sugar beet plants which are resistant to this herbicide. These and other objects will become increasingly apparent by reference to the following description and the drawings.

DESCRIPTION OF PREFERRED EMBODIMENTS

The present invention relates to a sugar beet plant material consisting of mutated cells with a mutated acetolactate synthase gene encoding the synthase, wherein the mutated cells have a resistance to an imidazolinone herbicide and wherein the resistance is transmittable by conventional cross-breeding of plants produced from the cells.

Further, the present invention relates to a method of producing a herbicide resistance in a sugar beet plant which comprises: exposing first cells of the sugar beet to an imidazolinone herbicide to which the first cells are sensitive in a culture medium; and selecting for second cells having the herbicide resistance, wherein the resistance can be transmitted by cross-breeding of plants containing the second cells.

Finally, the present invention relates to a method for imparting a herbicide resistance in a sugar beet which comprises: exposing first cells of sugar beet plant to an imidazolinone herbicide to which the first cells are sensitive in a culture medium; selecting for second cells having the herbicide resistance; growing a first plant from the second cells so that the plant has the herbicide resistance; and cross-breeding the first plants with second plants to produce crossed plants which have the herbicide resistance.

Figure 1:
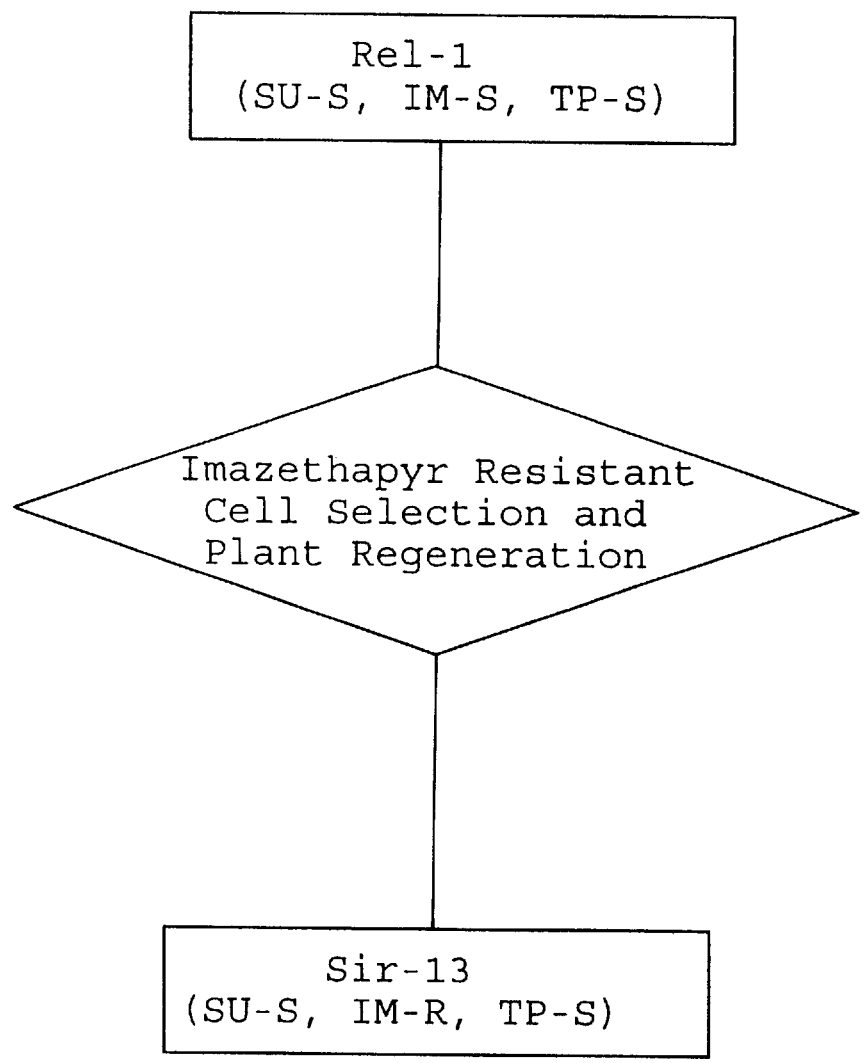
FIG. 1 is a schematic view of the method of the present invention for producing imidazolinone resistant sugar beet plants. R=Resistant; IM=imidazolinone; S=sensitive; SU=sulfonylurea; Sur=ALS allele dominant for SU-R, TP-R and IM-S; SIR-13=ALS allele dominant for SU-S, TP-S, and IM-R; TP=triazolopyrimidine. REL-1 was the starting material to obtain the imadazolinone resistance.

The sugar beet plant REL-1 (Regenerating, East Lansing-1) is available from Dr. Joseph Saunders, Research Geneticist, U.S. Department of Agriculture, East Lansing, Mich. and was released in 1987. It is available without cost. REL-1 is sensitive to imidazolinone (IM-S) sulfonylurea (SU-S) and triazolopyridine sulfonamide (TP-S) herbicides as shown in FIG. 1.

Using callus and suspension cultures, a line which was heterozygous for imidazolinone resistance (IMR) was developed. This cell line (seed) has been deposited with the American Type Culture Collection as ATCC 97534 on May 6, 1996 under the Budapest Treaty and is referred to herein as Sir-13. The cell line is available upon request by name and number, however, no license is granted because of such deposit. By breeding with elite sugar beet plant lines in particular *Beta vulgaris* L., especially commercially useful resistant sugar beet plants can be produced. Traditional breeding techniques can be used to transfer the imidazolinone resistance to other beets such as red beets.

Sugar beet plants resistant to the imidazolinone herbicides, specifically imazethapyr, solve the soil residue problem from the use of this herbicide in sugar beet growing areas. Currently, there is a 40-month waiting period between the use of that herbicide and the future use of that field for growing sugar beet plants. Secondly, a high level of imidazolinone herbicide resistance allows use of a imidazolinone for weed control in sugar beets.

The following Example 1 shows isolation and breeding of a novel sugar beet plant (Sir-13).

EXAMPLE 1

1. Selection of imidazolinone resistant sugar beet variants (SIR-13).

Description of Materials

Rel-1 (Regenerating East Lansing-1) is a highly regenerable male fertile sugar beet line used for initial cell selection for herbicideresistant mutant to the imidazolinones and is used as a sensitive control for most experiments. REL-1 was deposited with the American Type Culture Collection, Rockville, Md. on Feb. 18, 1997 as ATCC 97885.

Sir-13 This sugar beet isolate was developed by plating Rel-1 cells on imazethapyr-containing media. This variant is imidazolinone resistant, but not cross-resistant to the sulfonylureas.

Sir-30 A representative selected isolate which tends to be infertile. This was an aberrant result of the cell culture procedures.

a. Plants were selected as source materials for somaclonal selection based on their ability to generate callus under high cytokinin conditions (in B1 media) and regenerate shoots from callus.

Protocol for B1 media:
30 g $L^{-1}$ sucrose
100 mg $L^{-1}$ myo-inositol
1.65 g $L^{-1}$ $NH_4NO_3$
1.90 g $L^{-1}$ $KNO_3$
0.44 g $L^{-1}$ $CaCl_2 \cdot 2H_2O$
0.37 g $L^{-1}$ $MgSO_4 \cdot 7H_2O$
0.17 g $L^{-1}$ $KH_2PO_4$
6.2 mg $L^{-1}$ $H_3BO_3$
16.8 mg $L^{-1}$ $MnSO_4 \cdot H_2O$
10.6 mg $L^{-1}$ $ZnSO_4 \cdot 7H_2O$
0.88 mg $L^{-1}$ KI
0.25 mg $L^{-1}$ $Na_2MoO_4 \cdot 2H_2O$
0.025 mg $L^{-1}$ $CuSO_4 \cdot 5H_2O$
0.025 mg $L^{-1}$ $CoCl_2 \cdot 6H_2O$
37.3 mg $L^{-1}$ $Na_2EDTA$
27.8 mg $L^{-1}$ $FeSO_4 \cdot 7H_2O$
1 mg $L^{-1}$ thiamine
0.5 mg $L^{-1}$ pyridoxine
0.5 mg $L^{-1}$ nicotinic acid
1 mg $L^{-1}$ benzylaminopurine
pH 5.95

B1 solid media was autoclaved with 9 g $L^{-1}$ plant culture agar and modified with filter-sterilized herbicide stock solutions as needed for selection scheme. Agar media was poured into 15×100 mm disposable plastic petri dishes. B1 liquid media was added in 40 ml aliquots to 125 ml Erlenmeyer flasks and autoclaved for use in liquid suspension cultures.

Figure 2:
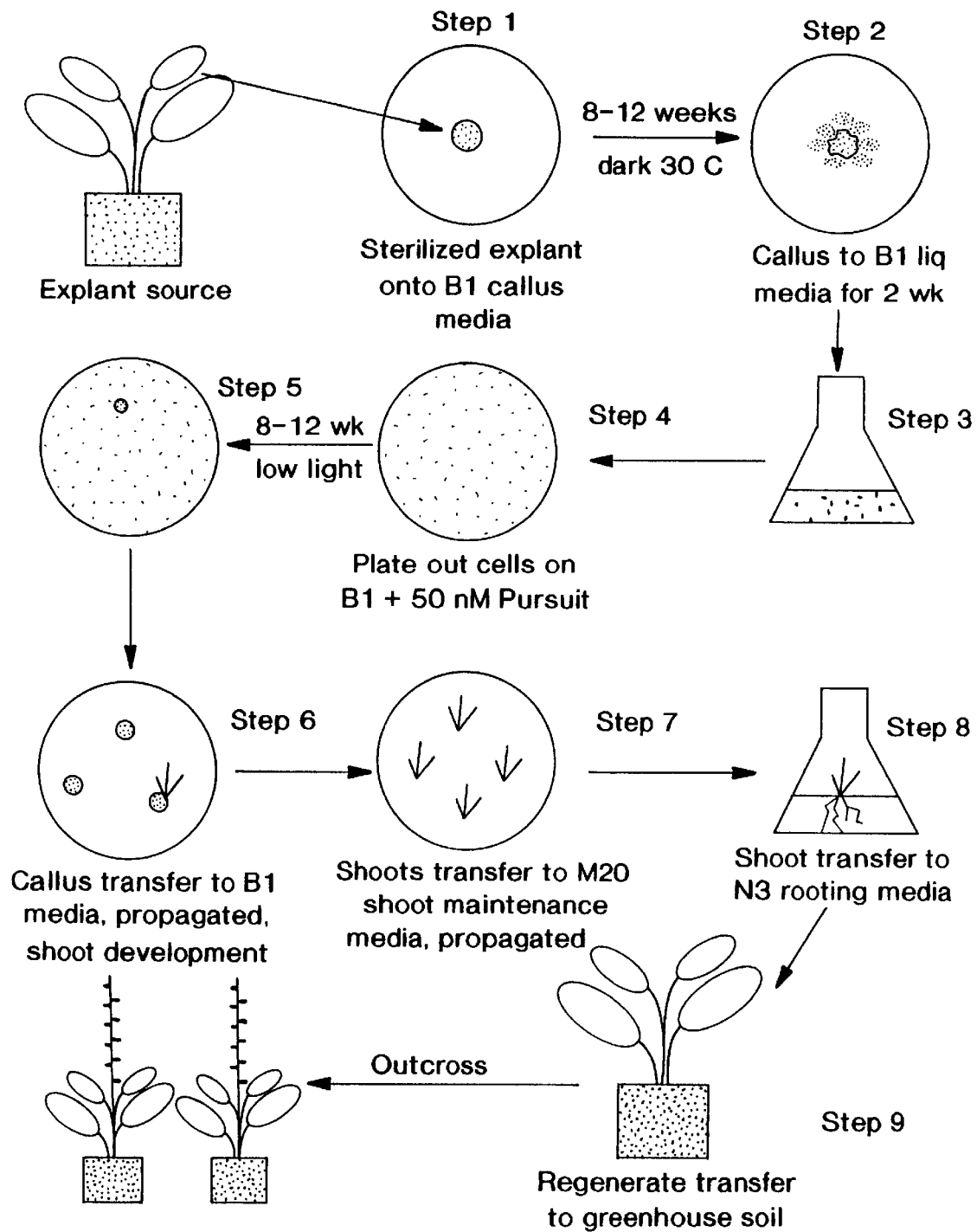
FIG. 2 is a flow diagram showing the detailed steps in producing a mutant sugar beet plant.

For selection of the imidazolinone resistant variant, Sir-13, the source material was Rel-1.

b. For selection of the imidazolinone resistant variant, a procedure was followed as shown in FIG. 2.

Leaf disk explants were prepared from rapidly expanding leaves of the source plant. The leaves were surface sterilized (step 1) by two successive 20-minute washes with 15% commercial bleach plus 0.025% Triton X-100 (T-9284, Sigma Chemical Co., St. Louis, Mo.). Leaves were rinsed twice with sterile deionized water. Leaf disks were cut using a flame-sterilized #3 cork borer.

Leaf disks were placed aseptically onto solid B1 media (step 2). Disks were incubated in the dark at 30° C. for 4–8 weeks until friable, white callus tissue had proliferated from the leaf disk. Callus tissue were separated mechanically with forceps and subsequently transferred to 125 ml Erlenmeyer flasks (step 3) containing 40 ml liquid B1 media. Flasks were placed onto a gyratory shaker at 50 Hz under low intensity fluorescent lighting (30 $\mu E/m^2$ s). Liquid cultures were subcultured with fresh B1 media after 1 week.

Two weeks after liquid culture initiation, cell clumps were separated using a cell dissociation sieve (Sigma CD-1) with a 60 mesh screen. Approximately two-thirds volume of the liquid media was removed following cell sedimentation. In step 4, cells were resuspended in remaining media and 1 ml aliquots were spread evenly over solid B1 media supplemented with 50 nM imazethapyr (PURSUIT, American Cyanamid, Wayne, N.J.) herbicide. Plates were wrapped and incubated in dim fluorescent light (5–10 $\mu E/m^2$ s) for 8–12 weeks.

c. At 50 nM imazethapyr concentration, all sensitive cells died. Cell clumps that survived and grew at this concentration are identified as possible resistant variants. In step 5, these cell clumps (1–3 mm in diameter) were transferred to fresh B1 solid media without herbicide and allowed to grow under low light (10–20 $\mu E/m^2$ s). Each putatively resistant variant was individually identified and maintained separately.

d. In step 6, white, friable callus was subdivided every 4–6 weeks to fresh B1 solid media until an individual shoot(s) grew from the callus. These shoots were transferred to shoot maintenance media (M20) as follows:

Protocol for M20 media:
30 g $L^{-1}$ sucrose
100 mg $L^{-1}$ myo-inositol
1.65 g $L^{-1}$ $NH_4NO_3$
1.90 g $L^{-1}$ $KNO^3$
0.44 g $L^{-1}$ $CaCl_2 \cdot 2H_2O$
0.37 g $L^{-1}$ $MgSO_4 \cdot 7H_2O$
0.17 g $L^{-1}$ $KH_2PO_4$
6.2 mg $L^{-1}$ $H_3BO_3$
16.8 mg $L^{-1}$ $MnSO_4 \cdot H_2O$
10.6 mg $L^{-1}$ $ZnSO_4 \cdot 7H_2O$
0.88 mg $L^{-1}$ KI
0.25 mg $L^{-1}$ $Na_2MoO_4 \cdot 2H_2O$
0.025 mg $L^{-1}$ $CuSO_4 \cdot 5H_2O$
0.025 mg $L^{-1}$ $CoCl_2 \cdot 6H_2O$
37.3 mg $L^{-1}$ $Na_2EDTA$
27.8 mg $L^{-1}$ $FeSO_4 \cdot 7H_2O$
1 mg $L^{-1}$ thiamine
0.5 mg $L^{-1}$ pyridoxine
0.5 mg $L^{-1}$ nicotinic acid
0.25 mg $L^{-1}$ benzylaminopurine
pH 5.95

M20 solid media was autoclaved with 9 g $L^{-1}$ plant culture agar and modified with filter-sterilized herbicide stock solutions as needed for selection scheme. Agar media was poured into 20×100 mm disposable plastic petri dishes.

Shoot cultures were maintained under 10–20 $\mu E/m^2$ s fluorescent lighting and propagated by dissecting shoot cultures with a scalpel blade. Candidate shoot cultures were propagated and assessed for level of resistance as described hereinafter.

2. Level of imidazolinone resistance in shoot culture.

In step 7, shoot cultures were assessed for herbicide resistance by placing three small, consistently sized shoot cuttings on each plate of M20 media supplemented with logarithmically increasing concentrations of imazethapyr herbicide ranging from 1 nM to 0.1 mM. Sir-13 culture responses were compared to that of shoot cultures of a sensitive control (Rel-1). Shoot cultures were maintained at 20 $\mu E/m^2$ s light intensity at 25° C. for 3 weeks. Shoot culture response was determined by rating shoot injury and fresh weight 3 weeks after transfer to selective media. Magnitude of herbicide resistance was determined by the ratio of resistant to sensitive $I_{50}$ values (the herbicide concentration causing 50 percent injury).

The cross resistance characteristics of each variant were determined in the manner above by substituting the herbicide used in the media. In shoot culture Sir-13 showed a 220 fold level of resistance to imazethapyr and showed no cross resistance to the sulfonylurea herbicide, chlorsulfuron or the triazolopyrimidine sulfonanilide herbicide, flumetsulam as shown in Table 1.

TABLE 1

Magnitude of shoot culture and ALS resistance and cross resistance.

| Clone | | Imazethapyr | Imazamethabenz | Imazaquin | AC299,263[1] | Chlorsulfuron[2] | Flumetsulam[3] |
|---|---|---|---|---|---|---|---|
| Rel-1 | Shoot culture $I_{50}$ | 18 nM | 800 nM | 40 nM | 30 nM | 2.5 nM | 28 nM |
|  | ALS $I_{50}$ | 2.7 μM | 430 nM (acid) | | | 10 nM | 150 nM |
| Sir-13 (Sir) | Shoot culture $I_{50}$ | 3.9 μM | >100 μM | 3.0 μM | 3.5 μM | 3.0 nM | 20 nM |
|  | R/S[4] | 200 X | >125 X | 75 X | 120 X | 1 X | 1 X |
|  | ALS $I_{50}$[5] | 400 μM | | | | 11 nM | |
|  | R/S | 150 X | | | | 1 X | |

[1]Imidazolinone (American Cyanamid, Wayne, NJ).
[2]Sulfonylurea = Glean (Dupont, Wilmington, DE)
[3]Triazolopyrimidine sulfonanilide (BROADSTRIKE, Dow Elanco, Indianapolis, IN).
[4]R/S = ratio of resistant to sensitive control $I_{50}$ value for the specific herbicide being tested.
[5]$I_{50}$ is the concentration of herbicide required to cause 50% injury to the shoot culture 3. Plant regeneration and breeding.

In step 8, shoot cultures of Sir-13 were regenerated to whole plants in a similar manner. Two weeks following previous shoot subculture, Sir-13 shoots were transferred to 125 ml Erlenmeyer flasks containing 40 ml N3 rooting media.

Protocol for N3 media:
30 g $L^{-1}$ sucrose
100 mg $L^{-1}$ myo-inositol
1.65 g $L^{-1}$ $NH_4NO_3$
1.90 g $L^{-1}$ $KNO_3$
0.44 g $L^{-1}$ $CaCl_2 \cdot 2H_2O$
0.37 g $L^{-1}$ $MgSO_4 \cdot 7H_2O$
0.17 g $L^{-1}$ $KH_2PO_4$
6.2 mg $L^{-1}$ $H_3BO_3$
16.8 mg $L^{-1}$ $MnSO_4 \cdot H_2O$
10.6 mg $L^{-1}$ $ZnSO_4 \cdot 7H_2O$
0.88 mg $L^{-1}$ KI
0.25 mg $L^1$ $Na_2MoO_4 \cdot 2H_2O$
0.025 mg $L^{-1}$ $CuSO_4 \cdot 5H_2O$
0.025 mg $L^{-1}$ $CoCl_2 \cdot 6H_2O$
37.3 mg $L^{-1}$ $Na_2EDTA$
27.8 mg $L^1$ $FeSO_4 \cdot 7H_2O$
1 mg $L^{-1}$ thiamine
0.5 mg $L^1$ pyridoxine
0.5 mg $L^{-1}$ nicotinic acid
3 mg $L^{-1}$ naphthalene acetic acid
pH 5.95

N3 media added in 40 ml aliquots to 125 ml Erlenmeyer flasks, 9 g $L^{-1}$ agar (0.45 g) added to each flask, and autoclaved for use in rooting of shoot cultures. Cultures were then transferred to 24 hour per day light under medium light intensity (40–60 μE/m² s) at 25° C. Roots generally formed 6–8 weeks later.

In step 9, rooted shoots ($R_o$ generation) were then transferred to Baccto (Michigan Peat Co., Houston, TX) potting mix in the greenhouse. In step 10, $R_o$ plants of Sir-13 were crossed with a smooth-root sugar beet called 293. $F_1$ seed from these crosses were selffertilized to yield $F_2$ seed. It was presumed that imidazolinone resistance was a dominant or semi-dominant monogenic trait. $F_2$ generation plants should be segregating in a 1 homozygous resistant: 2 heterozygous resistant: 1 homozygous sensitive ratio for imidazolinone resistance.

Sir-13 Inheritance as a Monogenic Dominant Trait

This ratio was examined by progeny testing each of the $F_2$ plants. For Sir-13, $F_2$ plants were allowed to self-fertilize and seed were collected separately from each plant. These progeny were planted in the greenhouse and sprayed at the 2–4 leaf stage with a ¼X field application rate of imazethapyr (PURSUIT) herbicide (0.0625 1b ai/A+1 qt/A SunIt-II (AGSCO Fargo)+1 qt/A 28% UAN (urea ammonium nitrate). This rate allows discrimination of plants that have 1 or 2 copies of the Sir-13 allele from sensitive plants.

Each of the Sir-13 families were categorized to homozygous resistant, heterozygous resistant, or homozygous sensitive based on progeny test segregation. The results clearly showed Sir-13 $F_2$ segregation fit a 1:2:1 ratio for the respective categories as shown in Table 2.

TABLE 2

| Parent Designation | Progeny Segregation Ratio | Number of $F_2$ Parents |
|---|---|---|
| Homozygous Resistant | All R | 12 |
| Heterozygous Resistant | 3R:1S | 35 |
| Homozygous Sensitive | All S | 15 |

These results suggest that Sir-13 is a monogenic dominant trait. The degree of dominance or semidominance has not been determined to date.

Figure 3:
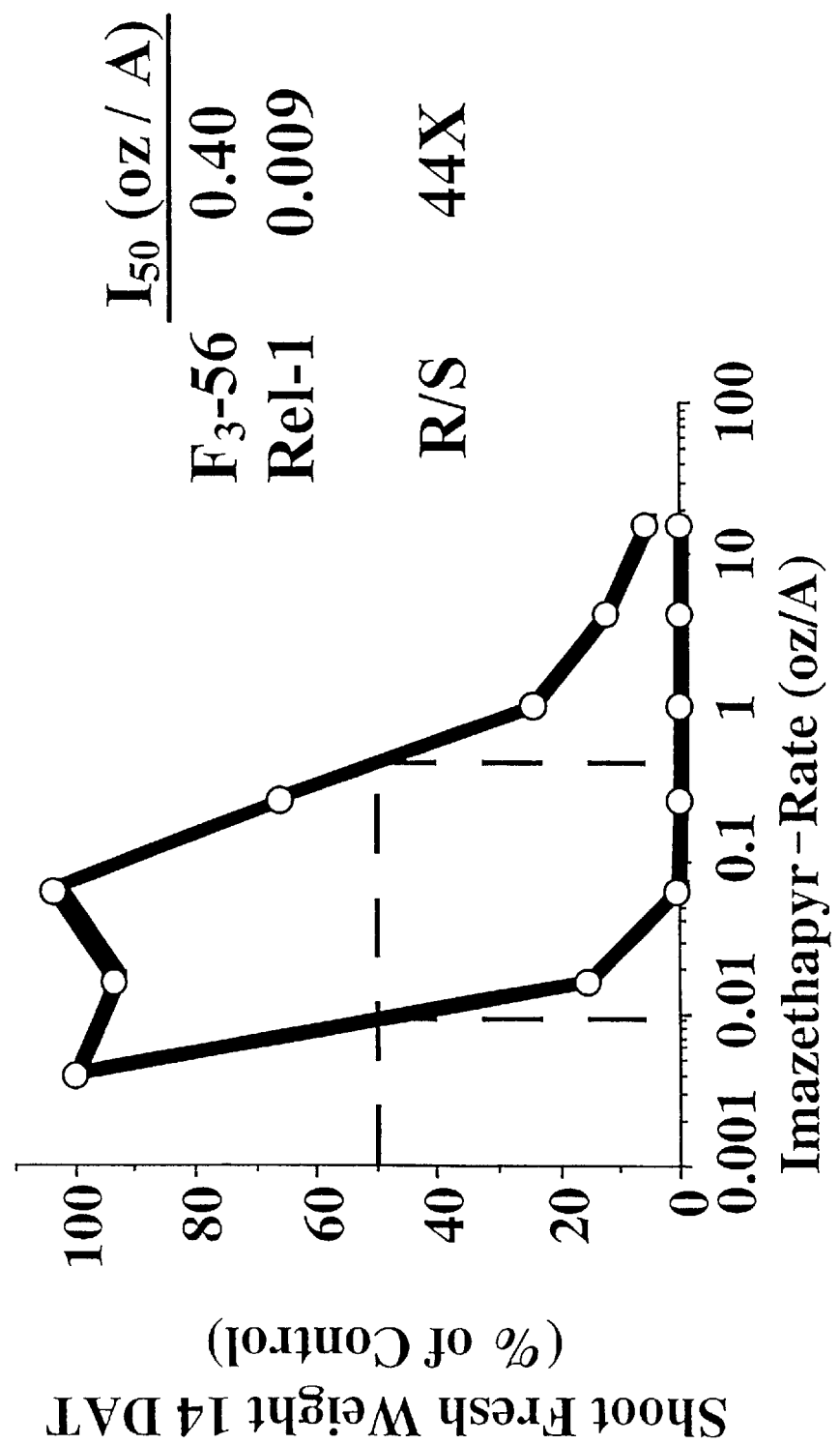
FIG. 3 is a graph showing imazethapyr resistance to a postemergence spray application to sugar beet plants.

4. Whole plant imidazolinone resistance Homozygous (nonsegregating) Sir-13 $F_2$ plants were self fertilized to produce homozygous Sir-13 $F_3$ seed. Rel-1 clones were allowed to self fertilize to produce sensitive $S_1$ seed. Seed were planted into Baccto potting mix in the greenhouse and thinned to one plant per pot 14 days after planting. Plants were sprayed at the 4–6 leaf stage with 0, 0.26, 1.1, 4.4, 17.5, 70, or 280 g active ingredient/ha imazethapyr (PURSUIT) or AC 299,263 (RAPTOR). All treatments were applied in a volume of 239 L/ha and included the following spray additives: SunIt-II at 1% by volume and 28% UAN at 1% by volume. Each treatment was replicated four times. Shoot fresh weights determined 20 days after treatment. Sir-13 and sensitive beet responses are shown in FIG. 3. Sir-13 homozygotes show 120 and 90 fold resistance to imazethapyr and AC 299,263, respectively.

5. ALS target enzyme response to imazethapyr

Standard procedures were utilized to partially purify ALS from rapidly expanding leaves of greenhousegrown sugar beet plants (Hart, et al, Weed Science 40:378–383 (1992)). Extracts from homozygous Sir-13 $F_3$ plants and Rel-1 $S_1$ seed were assayed for ALS activity in the presence of logarithmically increasing concentrations of imazethapyr. ALS activity was determined from leaf extracts of REL-1 and Sir-13 sugarbeet lines. Plants were grown in the greenhouse as described above to the four to six leaf stage. ALS activity from fresh extracts was determined in the presence of imazethapyr at logarithmically increasing concentrations. The methods and procedures used were modified from those outlined by Ray (Plant Physiol. 75:827–831 (1984)) and Shaner, et al. (Plant Physiol. 76:545–546 (1984)). Ten g of sugarbeet leaves were homogenized in 40 ml cold homogenization buffer (0.1 M $K_2HPO_4$, pH 7.5, 1 mM sodium pyruvate, 0.5 mM $MgCl_2$, 0.5 mM thiamine pyrophosphate, 10 µM of flavin adenine dinucleotide, 10% by vol glycerol) plus 2.5 g polyvinylpolypyrolidone. The homogenate was filtered through eight layers of cheesecloth and centrifuged at 27,000 g for 20 minutes. The supernatant was removed and brought to 50% saturation with $(NH_4)_2SO_4$. This solution was kept at 0° C. for 1 hour, then centrifuged at 18,000 g for 15 minutes, the pellet redissolved in 1 ml resuspension buffer (0.1 M $K_2HPO_4$, pH 7.5, 20 mM sodium pyruvate, 0.5 mM $MgCl_2$) and desalted on a Sephadex G-25 PD-10 column (Pharmacia, Inc., Piscataway, N.J.). The enzyme extracts were assayed immediately.

ALS activity was measured by adding 0.2 ml of enzyme preparation (diluted 3:1 with resuspension buffer) to 1.3 ml of reaction buffer (25 mM $K_2HPO_4$, pH 7.0, 0.625 mM $MgCl_2$, 25 mM sodium pyruvate, 0.625 mM thiamine pyrophosphate, 1.25 µM flavin adenine dinucleotide) and incubated at 35° C. for 1 hour. Reaction mixtures contained a final concentration of 0, 4, 40, 400, 4000, 40000, 400000, or 4000000 nM imazethapyr or 0, 0.9, 9, 90, 900, 9000, 90000 nM chlorsulfuron. The reaction was stopped by adding 50 µl of 6 N $H_2SO_4$ and incubating at 60° C. for 15 minutes. This procedure as described by Westerfield (J. Biol. Chem. 16:495–502 (1945)) also decarboxylates the ALS enzyme product, acetolactate, to form acetoin. A colored acetoin complex was formed by adding 1 ml 2.5% by weight a-naphthol and 0.25% by weight creatine in 2.5 N NaOH and incubating at 60° C. for 15 minutes.

Purchased acetoin was used as a standard for the colorimetric reaction. Acetoin concentrations were determined by measuring the absorption of the reaction solution at 530 nm. Experiments with each herbicide were repeated with three replications in each. Protein concentrations of the extracts was determined by the method of Bradford (Anal. Biochem. 72:248–254 (1976)) using bovine serum albumin for the standard curve.

Figure 4:
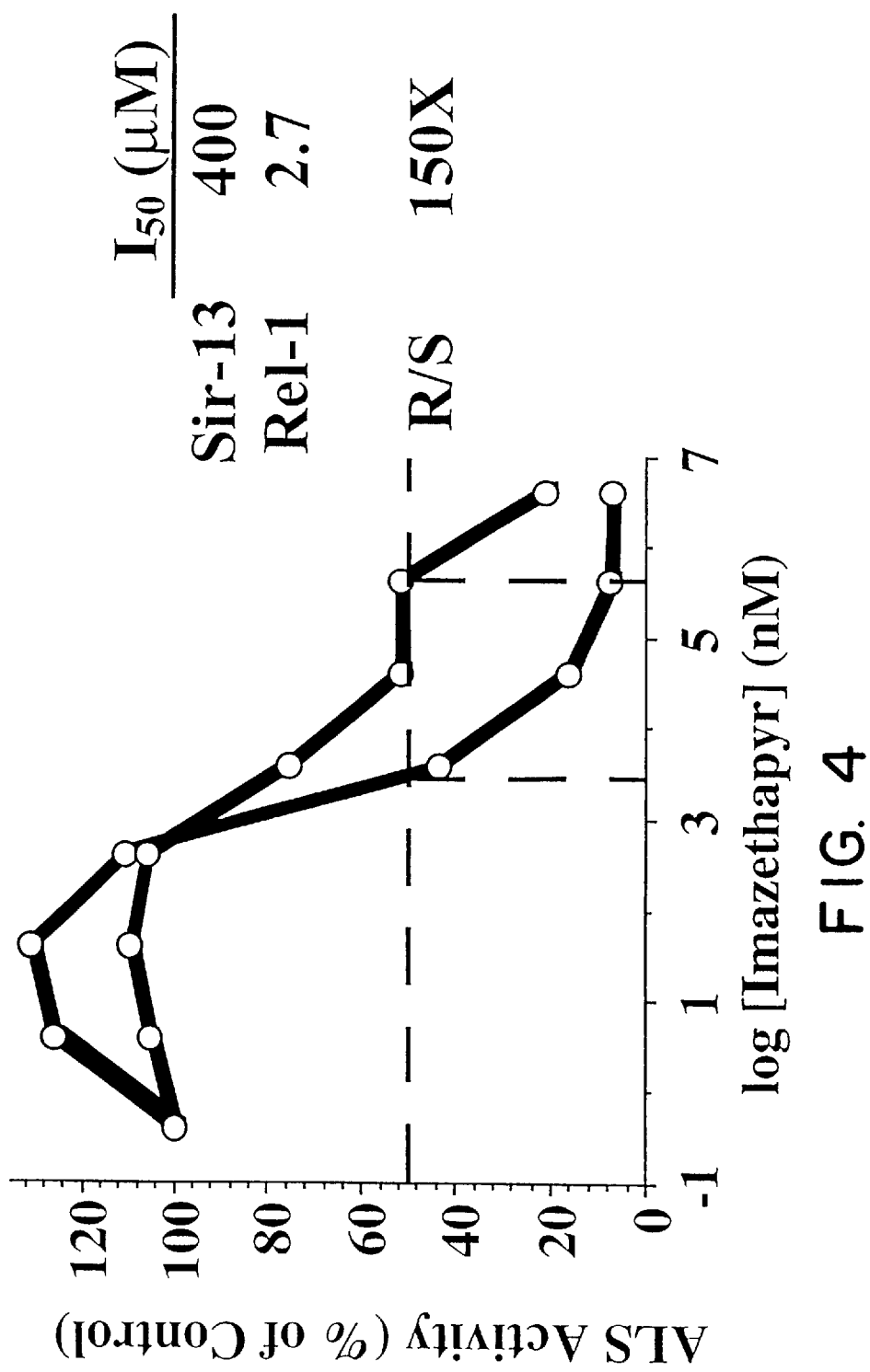
FIG. 4 is a graph showing imazethapyr resistance in an ALS assay in a cell culture.

Experiments were conducted twice and treatments replicated three times. FIG. 4 shows the response of ALS extracts from Sir-13 homozygote and the sensitive Rel-1. Sir-13 shows a 150-fold level of resistance to imazethapyr at the enzyme level (as determined by the ratio of $I_{50}$'s for the resistant and sensitive lines). FIG. 3 shows a 44 times resistance for the whole plant as discussed above.

6. ALS Gene Copy Number

Southern blot analysis was conducted to determine the number of ALS gene copies present in sensitive sugar beet. Genomic DNA was isolated from sensitive $F_3$ plants descended from the original Sir-13 mutant and analyzed using commonly practiced techniques (Current Protocols in Molecular Biology, J Wiley and Sons, New York (1991)). Likewise, genomic DNA from a commercial sugar beet variety was analyzed. In both sugar beet lines, a single copy of the ALS gene was detected. This data would indicate that all ALS enzyme activity of a homozygous mutant-type sugar beet would consist of the resistant enzyme form.

7. ALS Gene Mutation

To determine the molecular basis for ALS enzyme resistance, standard techniques were used to sequence two regions of the ALS gene where all previously reported herbicide resistance mutations have occurred (Current Protocols in Molecular Biology, J. Wiley and Sons, New York (1991)). The sugar beet ALS gene had previously been sequenced (U.S. Pat. No. 5,378,824) and Polymerase Chain Reaction (PCR) primers designed to amplify the two regions of the gene responsible for previously reported cases of plant herbicide resistance. Comparison of sequence data from resistant (Sir-13) and sensitive (Rel-1) sugar beets indicated a single nucleotide change from guanine to adenine at position 337 in the nucleotide sequence which results in a threonine for alanine substitution at position 113 in the sugar beet ALS amino acid sequence. This site has previously been implicated in imidazolinone resistance in cocklebur (Bernasconi et al., J. Biol. Chem. 270:17381–17385 (1995)) and for sulfonylurea resistance in yeast (U.S. Pat. No. 5,378,824). No other bases changes were observed from wild type nucleotide sequence in the two regions of the ALS gene examined.

It is intended that the foregoing description be only illustrative of the present invention and that the present invention be limited only by the hereinafter appended claims.

We claim:

1. A sugar beet plant material consisting of mutated cells with a mutated acetolactate synthase gene encoding the synthase wherein a nucleotide is modified from guanine to adenine at position 337, wherein the mutated cells have a resistance to an imidazolinone herbicide and wherein the resistance is transmittable by conventional cross-breeding of plants produced from the cells and the cells are regenerable to a plant.

2. The material of claim 1 which has been derived from sensitive cells of a parent sugar beet plant, designated as REL-1 and deposited as ATCC 97885, and having no resistance to the herbicide, by cultivation of the sensitive cells in a culture medium with the herbicide to select for the mutated cells.

3. The material of claim 1 in a deposit of a seed designated as ATCC 97534 (SIR-13).

4. The plant material of claim 1 as a seed or propagule of the seed.

5. A method of producing a herbicide resistance in a sugar beet plant which comprises:

(a) exposing first cells of the sugar beet to an imidazolinone herbicide to which the first cells are sensitive in a culture medium; and (b) selecting for second cells having the herbicide resistance with a mutated acetolactate synthase gene encoding the synthase wherein a nucleotide is modified from guanine to adenine at position 337, wherein the resistance can be transmitted by cross-breeding of plants containing the second cells.

6. The method of claim 5 wherein the second cells are derived from the first cells of a sugar beet plant designated as REL-1 and deposited as ATCC 97885.

7. The method of claim 5 wherein the second cells are in a deposit of a seed designated as ATCC 97534 (SIR-13).

8. A method for imparting a herbicide resistance in a sugar beet which comprises:

(a) exposing first cells of sugar beet plant to an imidazolinone herbicide to which the first cells are sensitive in a culture medium;

(b) selecting for second cells having the herbicide resistance;

(c) growing a first plant from the second cells so that the plant has the herbicide resistance with a mutated acetolactate synthase gene encoding the synthase wherein a nucleotide is modified from guanine to adenine at position 337; and (d) cross-breeding the first plants with second plants to produce crossed plants which have the herbicide resistance.

9. A method for imparting herbicide resistance to other beets which comprises:

(a) exposing first cells of sugar beet plant to an imidazolinone herbicide to which the first cells are sensitive in a culture medium;

(b) selecting for second cells having the herbicide resistance;

(c) growing a first plant from the second cells so that the plant has the herbicide resistance with a mutated acetolactate synthase gene encoding the synthase wherein a nucleotide is modified from guanine to adenine at position 337; and (d) cross-breeding the first plants with second plants to produce crossed plants which have the herbicide resistance.

10. The method of claim 8 wherein the first cells in step (a) are derived from a sugar beet designated as REL-1 and deposited as ATCC 97885.

11. The method of claim 8 wherein the second cells are in a deposit of a seed designated as ATCC 97534 (SIR-13).

12. A method for controlling weeds growing with sugar beet plants which comprises:

(a) planting in a field beet seeds containing cells with a mutated acetolactate synthase gene encoding the synthase, wherein a nucleotide is modified from guanine to adenine at position 337, wherein the mutated cells have a resistance to imidazolinone herbicides and wherein the resistance is transmitted by conventional cross-breeding of plants produced from the cells to produce the sugar beet plant; and (b) using an imidazolinone herbicide on the plant in the field to control weeds.

13. The method of claim 12 wherein the plant is derived from sensitive cells of a parent sugar beet plant, designated as REL-1 and deposited as ATCC 97885 and having no resistance to imidazolinone herbicides, by cultivation of the sensitive cells in a culture medium with the imidazolinone herbicide to select for the mutated cells.

14. The method of claim 12 wherein the plant is derived from a seed deposited as ATCC 97534 (SIR-13).

* * * * *